(12) United States Patent
Chiou et al.

(10) Patent No.: US 9,420,961 B2
(45) Date of Patent: Aug. 23, 2016

(54) PHYSIOLOGICAL SIGNAL COLLECTION UNIT AND DETECTOR THEREOF

(75) Inventors: Jin-Chern Chiou, Hsinchu (TW); Yu-Chieh Huang, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 257 days.

(21) Appl. No.: 13/473,523

(22) Filed: May 16, 2012

(65) Prior Publication Data

US 2013/0030270 A1    Jan. 31, 2013

(30) Foreign Application Priority Data

Jul. 26, 2011  (TW) .............................. 100126389 A

(51) Int. Cl.
*A61B 5/1455* (2006.01)
*A61B 5/0476* (2006.01)
*A61B 5/00* (2006.01)

(52) U.S. Cl.
CPC ........... *A61B 5/0476* (2013.01); *A61B 5/14553* (2013.01); *A61B 5/6803* (2013.01); *A61B 5/6814* (2013.01)

(58) Field of Classification Search
USPC .................................................. 600/310–344
See application file for complete search history.

(56) References Cited

U.S. PATENT DOCUMENTS

| 7,899,510 B2 * | 3/2011 | Hoarau .......................... 600/344 |
| 2006/0058594 A1 * | 3/2006 | Ishizuka et al. ............... 600/310 |
| 2007/0106170 A1 * | 5/2007 | Dunseath et al. ............. 600/544 |

* cited by examiner

*Primary Examiner* — Tse Chen
*Assistant Examiner* — Marjan Fardanesh
(74) *Attorney, Agent, or Firm* — DLA Piper LLP (US)

(57) ABSTRACT

A physiological signal collection unit is for use with a physiological signal measuring apparatus to measure physiological signals from an anatomical part of a test subject, in which the anatomical part is covered with hair. The physiological signal collection unit includes a detector and a wearable member. The detector includes a circuit substrate defining a substrate-through-hole to permit hair strands to extend through, an electrical connector, and at least one signal collecting component. The wearable member is to be worn on the anatomical part of the test subject, and is formed with a through-hole having a size smaller than size of the circuit substrate. The through-hole permits the hair strands extending through the circuit substrate to extend through the wearable member.

20 Claims, 4 Drawing Sheets

PHYSIOLOGICAL SIGNAL COLLECTION UNIT AND DETECTOR THEREOF

CROSS-REFERENCE TO RELATED APPLICATION

This application claims priority to Taiwanese Application No. 100126389, filed on Jul. 26, 2011.

BACKGROUND OF THE INVENTION

1. Field of the Invention

The invention relates to a physiological signal measuring tool, and more particularly to a physiological signal collection unit and a detector that are adapted for use on an anatomical part covered with hair.

2. Description of the Related Art

Current applications of physiological signal collection units for the head, such as photoplethysmography (PPG) measurement, oxyhemoglobin and deoxyhemoglobin measurement of the brain, and regional cerebral oxygen saturation ($rSO_2$) measurement of the brain, could be used to analyze blood flow of the brain. Technically, the current applications use lighting components (such as light emitting diodes) to illuminate the anatomical part of a test subject, and use light sensing components (such as phototransistors or photodiodes) to receive light reflected or transmitted from the anatomical part to proceed with signal processing and analysis.

However, the scalp is covered with hair, so that when proceeding with the PPG measurement of the brain, hemoglobin and $rSO_2$ detection of the brain, both emission and reception of the light will be interfered by hair to cause scattering that affects intensity, resulting in inability to obtain a correct physiological signal. Most of current improvements in the relevant field involve increasing the power of the lighting devices to ensure the intensity of the received light. However, illumination using high power light may result in temperature variations of the skin tissue and cause vasodilation that affects blood flow, or even damage to skin and brain tissues. On the other hand, power consumption and effect of hair denseness on the reflected light intensity are also problems.

In addition, an electroencephalogram (EEG) measuring apparatus includes an EEG cap and a plurality of electrodes to measure EEG. To ensure the signal transmission, conductive adhesive must be used on each contact between the electrodes and the scalp. However, the process of wearing the current EEG measuring apparatus is complicated and the hair of the test subject must be washed to remove the conductive adhesive after finishing with the measurement.

SUMMARY OF THE INVENTION

Therefore, an object of the present invention is to provide a physiological signal collection unit that can overcome the above drawbacks of the prior art.

According to one aspect of the present invention, a physiological signal collection unit is adapted for use with a physiological signal measuring apparatus to measure physiological signals from an anatomical part of a test subject. The anatomical part is covered with hair. The physiological signal collection unit comprises a detector and a wearable member. The detector includes a circuit substrate, an electrical connector, and at least one signal collecting component. The circuit substrate has one side to be disposed proximate to the anatomical part and an opposite side opposite to the one side, and defines a substrate-through-hole that is configured to permit hair strands on the anatomical part to extend therethrough. The electrical connector is disposed on the circuit substrate and is configured to permit electrical connection between the detector and the physiological signal measuring apparatus. The signal collecting component is disposed on the circuit substrate and is responsive to control from the physiological signal measuring apparatus for measuring the physiological signals from the anatomical part of the test subject. The wearable member is configured to be worn on the anatomical part of the test subject, is disposed at the opposite side of the test subject, and is formed with a through-hole having a size smaller than size of the circuit substrate. The through-hole permits the hair strands extending through the circuit substrate to extend through the wearable member.

Another object of the present invention is to provide a detector of the physiological signal collection unit.

According to another aspect of the present invention, a detector is for contacting an anatomical part of a test subject to measure physiological signals therefrom. The anatomical part is covered with hair. The detector comprises a circuit substrate, an electrical connector, and at least one signal collecting component. The circuit substrate has one side to be disposed proximate to the anatomical part and an opposite side opposite to the one side, and defines a substrate-through-hole that is configured to permit hair strands on the anatomical part to extend therethrough. The electrical connector is disposed on the circuit substrate. The signal collecting component is disposed on the circuit substrate and is controllable to measure the physiological signals from the anatomical part of the test subject.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
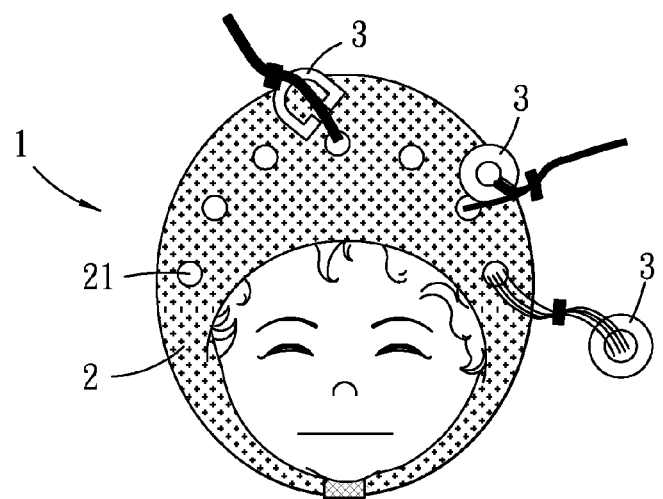
FIG. 1 is a schematic diagram showing how the preferred embodiment of the physiological signal collection unit according to the present invention is worn by a test subject.
Figure 6:
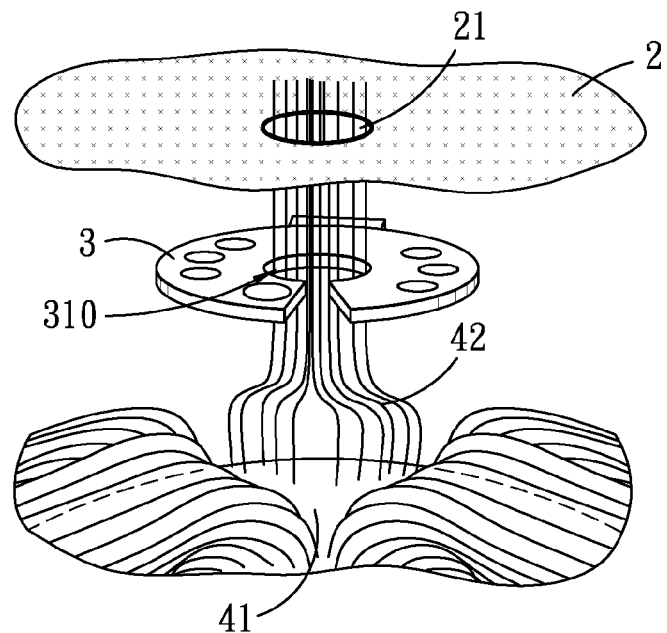
FIG. 6 is a fragmentary schematic diagram to illustrate how hair strands are extended through the detector of the preferred embodiment.
Figure 7:
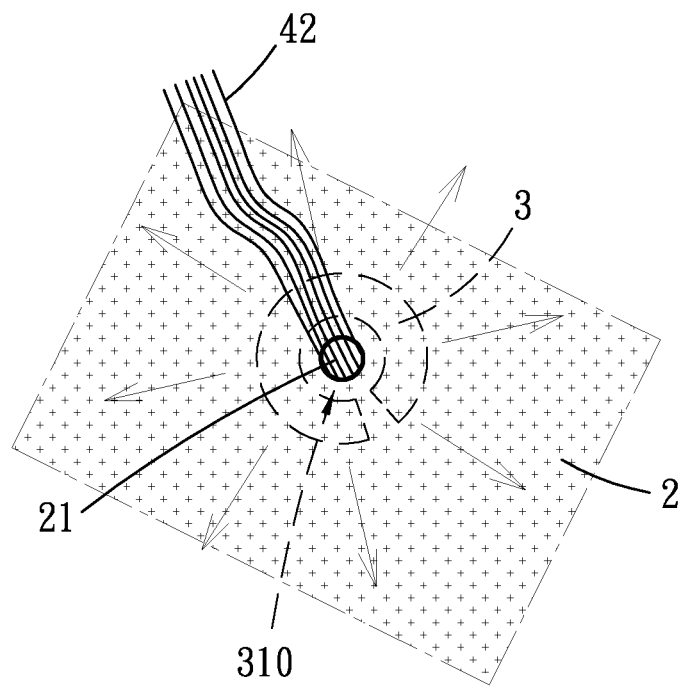
FIG. 7 is a schematic view to illustrate the detector of the preferred embodiment in a state of use.

FIG. 1 and FIG. 6 illustrate a physiological signal collection unit 1 of the preferred embodiment according to the present invention, which is for use with a physiological measuring apparatus (not shown), such as a photoplethysmography (PPG) measuring apparatus, a measuring apparatus for regional cerebral oxygen saturation ($rSO_2$) of the brain, and an electroencephalogram (EEG) measuring apparatus. The physiological signal collection unit 1 is used to measure physiological signals from an anatomical part 41 of a test subject. The anatomical part 41 is covered with hair 42, and is exemplified using the human head.

The physiological signal collection unit 1 of the preferred embodiment includes a wearable member 2 and a plurality of detectors 3. In this embodiment, the wearable member 2 is in a form of a headgear, such as a head cap, a kerchief or a headstrap, so as to be worn on the anatomical part 41, and is formed with at least one through-hole 21. Preferably, at least a portion of the wearable member 2 formed with the through hole 21 is made of stretchable fabric.

Figure 2:
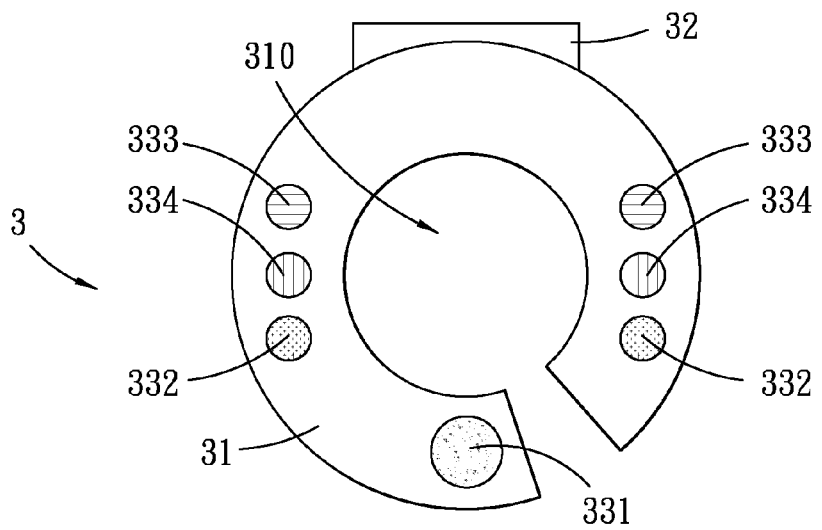
FIG. 2 is a schematic view showing a detector of the preferred embodiment.
Figure 3:
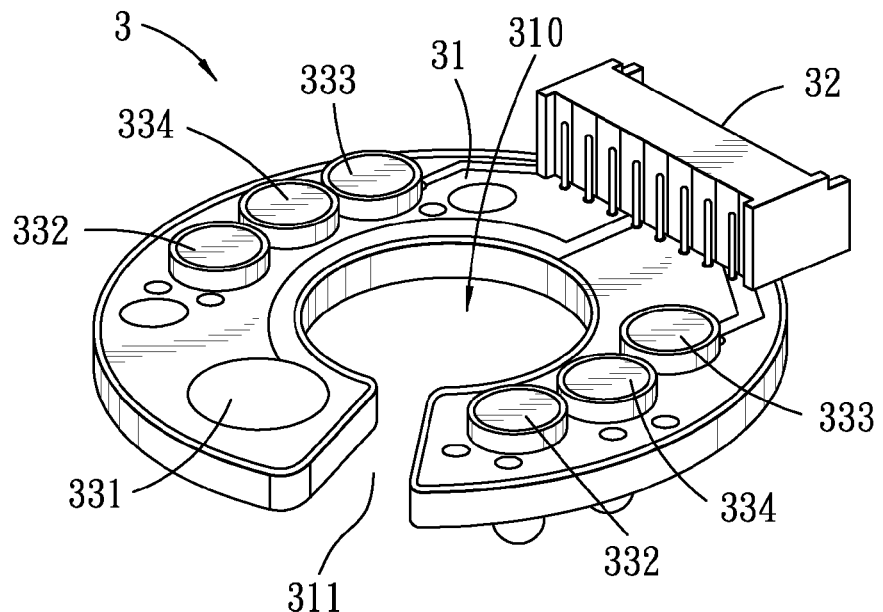
FIG. 3 is a perspective view showing the detector of the preferred embodiment.

Referring to FIG. 2 and FIG. 3, each detector 3 includes a circuit substrate 31 defining a substrate-through-hole 310, an electrical connector 32 disposed on the circuit substrate 31, and a plurality of signal collecting components disposed on the circuit substrate 31. In this embodiment, the signal collecting components include an electrical signal sensing electrode 331, two red light emitting diodes 332 and two near infrared light emitting diodes 333 that serve as light emitting components, and two photodiodes 334 or phototransistors that serve as light sensing components and that are each disposed between one of the red light emitting diodes 332 and one of the near infrared light emitting diodes 333. However, the present invention is not limited in the specific combination of the signal collecting components of this embodiment. For example, if the physiological signal collection unit 1 is configured for use only with the EEG measuring apparatus, the detector 3 only requires the electrical signal sensing electrode 331. In another example, if the physiological signal collection unit 1 is configured for use only with the PPG measuring apparatus, the detector 3 only requires at least one kind of the red light emitting diodes 332 and the near infrared light emitting diodes 333, and the photodiodes 334. In yet another example, if the physiological signal collection unit 1 is configured for use with the measuring apparatus for the $rSO_2$ of the brain, the detector 3 requires two or more than two kinds of the lighting sources with different wavelengths, such as the red light emitting diodes 332 and the near infrared light emitting diodes 333, and the photodiodes 334 each disposed between two kinds of the lighting sources. Moreover, the number of the signal collecting components in a detector 3 is not limited to the disclosed embodiment.

Figure 4:
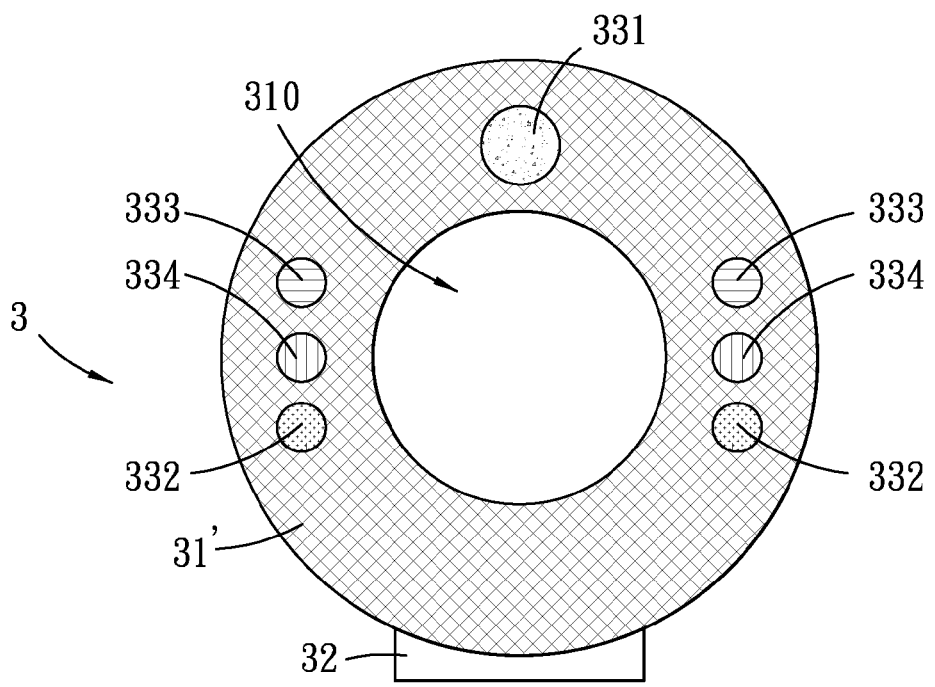
FIG. 4 is a schematic view showing a modification of the detector of the preferred embodiment.
Figure 5:
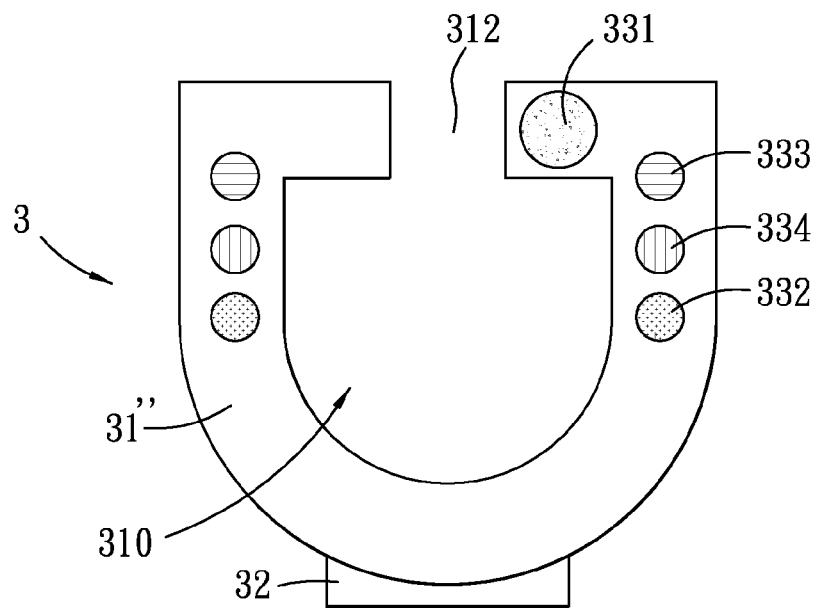
FIG. 5 is a schematic view showing another modification of the detector of the preferred embodiment.

The circuit substrate 31 shown in the embodiment of FIG. 2 and FIG. 3 is C-shaped, and has a first portion formed with a notch 311 in spatial communication with the substrate-through-hole 310 and a second portion opposite to the first portion. The electrical connector 32 is disposed at the second portion adjacent to an outer peripheral edge of the circuit substrate 31. As shown in FIG. 4, the circuit substrate 31' could be in a form of a ring, and the electrical connector 32 is disposed adjacent to an outer peripheral edge of the circuit substrate 31'. As shown in FIG. 5, the circuit substrate 31" could be U-shaped and could have a first portion formed with an opening 312 in spatial communication with the substrate-through-hole 310 and a second portion opposite to the first portion. The electrical connector 32 is disposed at the second portion adjacent to an outer peripheral edge of the circuit substrate 31". The shape of the circuit substrate is not limited as long as the substrate-through-hole 310 is defined therein.

Referring to FIG. 1, FIG. 3, FIG. 6 and FIG. 7, the size of the circuit substrate 31 is not smaller than the size of the through-hole 21 of the wearable member 2, i.e., the size of the through-hole 21 is smaller than the size of the circuit substrate 31. When using the physiological signal collection unit 1, the wearable member 2 is first worn on the anatomical part 41 with strands of the hair 42 being extended through one of the through-holes 21 of the wearable member 2. The strands of hair 42 are then tied together in a bundle by extending through the substrate-through-hole 310 of the circuit substrate 31. The detector 3 is then extended through the wearable member 2 via the through-hole 21 (which is in a stretchable part of the wearable member 2) such that one side of the circuit substrate 31 is disposed proximate to the anatomical part 41 and such that the wearable member 2 is disposed at an opposite side of the circuit substrate 31 opposite to the one side. At this time, the signal collecting components on the circuit substrate 31 could operate with less interference from the hair 42 on the anatomical part 41. Moreover, the electrical connector 32 could be accessed via the through-hole 21 to facilitate plugging connection with the physiological signal measuring apparatus, so that the physiological signals could be obtained with the operation of the signal collecting components in response to control from the physiological signal measuring apparatus.

As described above, through the use of the detectors 3 and the wearable member 2 according to this invention, obstruction and interference by hair 42 covering the anatomical part 41 of the test subject can be minimized, such that the electrical signal sensing electrode 331, the light emitting components, and the light sensing components could operate on the skin of the anatomical part 41 with higher precision. When used with the EEG measuring apparatus, the present invention dispenses with a complicated wearing process and use of conductive adhesive.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A physiological signal collection unit for use with a physiological signal measuring apparatus to measure physiological signals from an anatomical part of a test subject, the anatomical part being covered with hair, said physiological signal collection unit comprising:
   a detector including
     a circuit substrate having one side to be disposed proximate to the anatomical part and an opposite side opposite to said one side, and defining at least two substrate-through-hole with each substrate-through-hole being adjacent each signal collecting component,
     an electrical connector disposed on said circuit substrate and configured to permit electrical connection between said detector and the physiological signal measuring apparatus, and
     at least two signal collecting components disposed on said circuit substrate and responsive to control from the physiological signal measuring apparatus for measuring the physiological signals from the anatomical part of the test subject; and
   a wearable member configured to be worn on the anatomical part of the test subject, to be disposed at said opposite side of said circuit substrate, and formed with a through-hole that is to correspond in position to said circuit substrate and that has a size smaller than size of said circuit substrate;
   wherein said substrate-through-holes are configured to permit hair strands on the anatomical part that correspond in position to each of said signal collecting components to extend therethrough;
   wherein said through-hole of said wearable member permits the hair strands extending through said circuit substrate to extend through said wearable member.

2. The physiological signal collection unit as claimed in claim 1, wherein said circuit substrate is in a form of a ring, and said electrical connector includes a connector housing disposed adjacent to an outer peripheral edge of said circuit substrate.

3. The physiological signal collection unit as claimed in claim 1, wherein said circuit substrate is C-shaped and has a first portion formed with a notch in spatial communication with said substrate-through-hole and a second portion opposite to said first portion, said electrical connector including a connector housing disposed at said second portion adjacent to an outer peripheral edge of said circuit substrate.

4. The physiological signal collection unit as claimed in claim 1, wherein said circuit substrate is U-shaped and has a first portion formed with an opening in spatial communication with said substrate-through-hole and a second portion opposite to said first portion, said electrical connector including a connector housing disposed at said second portion adjacent to an outer peripheral edge of said circuit substrate.

5. The physiological signal collection unit as claimed in claim 1, wherein said signal collecting component is an electrical signal sensing electrode.

6. The physiological signal collection unit as claimed in claim 1, comprising two of said signal collecting components, one of said signal collecting components being a light emitting component, the other one of said signal collecting components being a light sensing component disposed adjacent to said light emitting component.

7. The physiological signal collection unit as claimed in claim 1, comprising three of said signal collecting components, a first one of said signal collecting components being a red light emitting diode, a second one of said signal collecting components being a near infrared light emitting diode, a third one of said signal collecting components being a light sensing component disposed adjacent to said red light emitting diode and said near infrared light emitting diode.

8. The physiological signal collection unit as claimed in claim 7, wherein said light sensing component is disposed between said red light emitting diode and said near infrared light emitting diode.

9. The physiological signal collection unit as claimed in claim 1, comprising four of said signal collecting components, a first one of said signal collecting components being a red light emitting diode, a second one of said signal collecting components being a near infrared light emitting diode, a third one of said signal collecting components being a light sensing component disposed adjacent to said red light emitting diode and said near infrared light emitting diode, a fourth one of said signal collecting components being an electrical signal sensing electrode.

10. The physiological signal collection unit as claimed in claim 1, wherein a portion of said wearable member formed with said through-hole is stretchable such that said circuit substrate is extendible through said through-hole when said portion of said wearable member is stretched while said wearable member is worn on the anatomical part.

11. The physiological signal collection unit as claimed in claim 1, wherein said wearable member is in a form of a headgear.

12. The physiological signal collection unit as claimed in claim 11, wherein said headgear is one of a head cap, a kerchief and a headstrap.

13. A detector for contacting an anatomical part of a test subject to measure physiological signals therefrom, the anatomical part being covered with hair, said detector comprising:
a circuit substrate having one side to be disposed proximate to the anatomical part and an opposite side opposite to said one side, and defining at least two substrate-through-holes with each substrate-through hole being adjacent each signal connecting component;
an electrical connector including a connector housing disposed on said circuit substrate; and
at least two signal collecting components disposed on said circuit substrate and controllable to measure the physiological signals from the anatomical part of the test subject,
wherein said substrate-through-holes are configured to permit hair strands on the anatomical part that correspond in position to each of said signal collecting components to extend therethrough.

14. The detector as claimed in claim 13, wherein said circuit substrate is in a form of a ring, and said connector housing is disposed adjacent to an outer peripheral edge of said circuit substrate.

15. The detector as claimed in claim 13, wherein said circuit substrate is C-shaped and has a first portion formed with a notch in spatial communication with said substrate-through-hole and a second portion opposite to said first portion, said connector housing being disposed at said second portion adjacent to an outer peripheral edge of said circuit substrate.

16. The detector as claimed in claim 13, wherein said circuit substrate is U-shaped and has a first portion formed with an opening in spatial communication with said substrate-through-hole and a second portion opposite to said first portion, said connector housing being disposed at said second portion adjacent to an outer peripheral edge of said circuit substrate.

17. The detector as claimed in claim 13, wherein said signal collecting component is an electrical signal sensing electrode.

18. The detector as claimed in claim 13, comprising two of said signal collecting components, one of said signal collecting components being a light emitting component, the other one of said signal collecting components being a light sensing component disposed adjacent to said light emitting component.

19. The detector as claimed in claim 13, comprising three of said signal collecting components, a first one of said signal collecting components being a red light emitting diode, a second one of said signal collecting components being a near infrared light emitting diode, a third one of said signal collecting components being a light sensing component disposed between said red light emitting diode and said near infrared light emitting diode.

20. The detector as claimed in claim 13, comprising four of said signal collecting components, a first one of said signal collecting components being a red light emitting diode, a second one of said signal collecting components being a near infrared light emitting diode, a third one of said signal collecting components being a light sensing component disposed adjacent to said red light emitting diode and said near infrared light emitting diode, a fourth one of said signal collecting components being an electrical signal sensing electrode.

* * * * *